United States Patent
Polack et al.

(12)

(10) Patent No.: US 6,521,449 B1
(45) Date of Patent: Feb. 18, 2003

(54) GENE CONSTRUCT AND ITS USE

(75) Inventors: Axel Polack, München (DE); Konstanze Hörtnagel, München (DE); Jürgen Wolf, Köln (DE); Susanne Mücke, Köln (DE)

(73) Assignee: GSF-Forschungszentrum für Umwelt und Gesundheit GmbH (DE)

( * ) Notice: Subject to any disclaimer, the term of this patent is extended or adjusted under 35 U.S.C. 154(b) by 0 days.

(21) Appl. No.: 09/434,574

(22) Filed: Nov. 4, 1999

Related U.S. Application Data

(63) Continuation of application No. 08/713,059, filed on Sep. 12, 1996, now abandoned.

(30) Foreign Application Priority Data

Nov. 7, 1995 (DE) .......................................... 195 41 450

(51) Int. Cl.$^7$ .......................... C12N 15/63; C12N 15/85; C12N 15/86; C07H 21/04; A61K 48/00; A61K 9/127

(52) U.S. Cl. .................. 435/320.1; 435/325; 536/24.1; 530/350; 424/450; 514/44

(58) Field of Search .............................. 435/320.1, 458, 435/440, 325; 530/350; 536/23.5, 23.4; 424/450; 514/2, 44

(56) References Cited

U.S. PATENT DOCUMENTS

| | | | |
|---|---|---|---|
| 4,939,088 A | 7/1990 | Young et al. | ............. 435/69.51 |
| 5,350,683 A | 9/1994 | Sims et al. | ................. 435/69.1 |
| 5,877,397 A | * 3/1999 | Lonberg | ........................ 800/2 |

FOREIGN PATENT DOCUMENTS

| | | |
|---|---|---|
| EP | 0 292 879 A2 | 5/1988 |
| WO | WO 90/10077 | 9/1990 |

OTHER PUBLICATIONS

Widlak, Piotr, et al. Interactions of the matrix attachment region of DNA with the matrix proteins from the copper preincubated liver nuclei, 1995, vol. 42, No. 2. p. 205–210.*
Orkin, et al.: Report and Recommendations of the Panel to Assess the NIH Investment in Research on Gene Therapy, www.nih.gov Dec. 1995.*
Verma, M. et al.: Gene Therapy–promises, problems and prospects, Nature vol. 389, Sep. 1997, pp. 239–242.*
Eck, S.L. et al. , 1996, Ch. 5. Gene Based Therapy,Goodman & Gillman's The Pharmacological basis of Therapeutics. p. 77–101ck, et al.*
Fulton, et al., "Kappa immunoglobulin promoters and enhancers display developmentally controlled interactions" *Nucleic Acids Research* 21:4941–4947 (1993).
Hagman, et al., "A novel enhancer in the immunoglobulin λ locus is duplicated and functionally independent of NFκB" *Genes& Development* 4:978–992 (1990).
Hörtnagel, et al., "The role of immunoglobulin λ elements in c–myc activation" *Oncogene* 10:1393–1401 (1995).
Kempkes, et al., "Immortalization of human primary B lymphocytes in vitro with DNA" *Proc. Natl. Acad. Sci.* 92:5875–5879 (1995).
Meyer, et al., "Activation of the immunoglobulin λ3 enhancer in pre–B cells correlates with the suppression of a nuclear factor binding to a sequence flanking the active core" *Nucleic Acids Research* 22:1576–1582 (1994).
Polack, et al., "Regulatory elements in the immunoglobulin kappa locus induce c–myc activation and the promoter shift in Burkitt's lymphoma cells" *EMBO Journal* 12:913–3920 (1993).
Sutcliffe, J. G., "Complete Nucleotide Sequence of the *Escherichia coli* Plasmid pBR322" *Cold Spring Harbor Symposia on Quantitative Biology* 43:77–90 (1979).
Bich–Thuy, L. and Queen, C., "An enhancer associated with the mouse immunoglobulin λ1gene is specific for λ light chain producing cells", Nucleic Acid Research, (1989) 17(13): 5307–5321.
Engelhardt, J. F. et al., "Retrovirus Vector–Targeted Inducible Expression of Human β–Interferon Gene to B–Cells", Virology (1990) 178: 413–428.
Jensen, U. B. et al., "Gene Transfer into Cultured Human Epidermis and its Transplantation onto Immunodeficient Mice: An Experimental Model for Somatic Gene Therapy", *J. Investigative Dermatology* (1994) 103(3): 391–394.
Maxwell, I. H. et al., "Expression of the Diphtheria Toxin A–Chain Coding Sequence under the Control of Promoters and Enhancers from Immunoglobulin Genes as a Means of Directing Toxicity to B–Lymphoid Cells", Cancer Research (1991), 51: 4299–4304.
Middleton, T and Sugden, B., "Retention of Plasmid DNA in Mammalian Cells Is Enhanced by Binding of the Epstein–Barr Virus Replication Protein EBNA1",*J. Virology*, (1994) 68(6): 4067–4071.
Mocikat, R. et al., "Differential interactions between the immunoglobulin heavy chain $\mu$ intron and 3' enhancer",*Eur. J. Immunol.* (1995) 25:3195–3198.
Mocikat, R. et al., "The effect of the rat immunoglobulin heavy–chain 3' enhancer is position dependent", Gene, (1993) 136: 349–353.
European Search Report dated Apr. 24, 1998.

* cited by examiner

*Primary Examiner*—Michael C. Wilson
(74) *Attorney, Agent, or Firm*—Bingham McCutchen LLP; David W. Maher

(57) ABSTRACT

Compositions of matter and methods for expressing a polypeptide are provided. In one aspect, a gene construct is provided that comprises an enhancer comprising particular elements or combinations of elements from the immunoglobulin κ locus, the immunoglobulin heavy chain $\mu$ locus, and the immunoglobulin λ locus, and a promoter and polyadenylation site linked to a nucleotide sequence encoding a polypeptide from a select group. Cells comprising the gene construct, processes for producing such cells, and processes for producing the polypeptide encoded by the gene construct from such cells are also provided.

36 Claims, 3 Drawing Sheets

Figure 1:
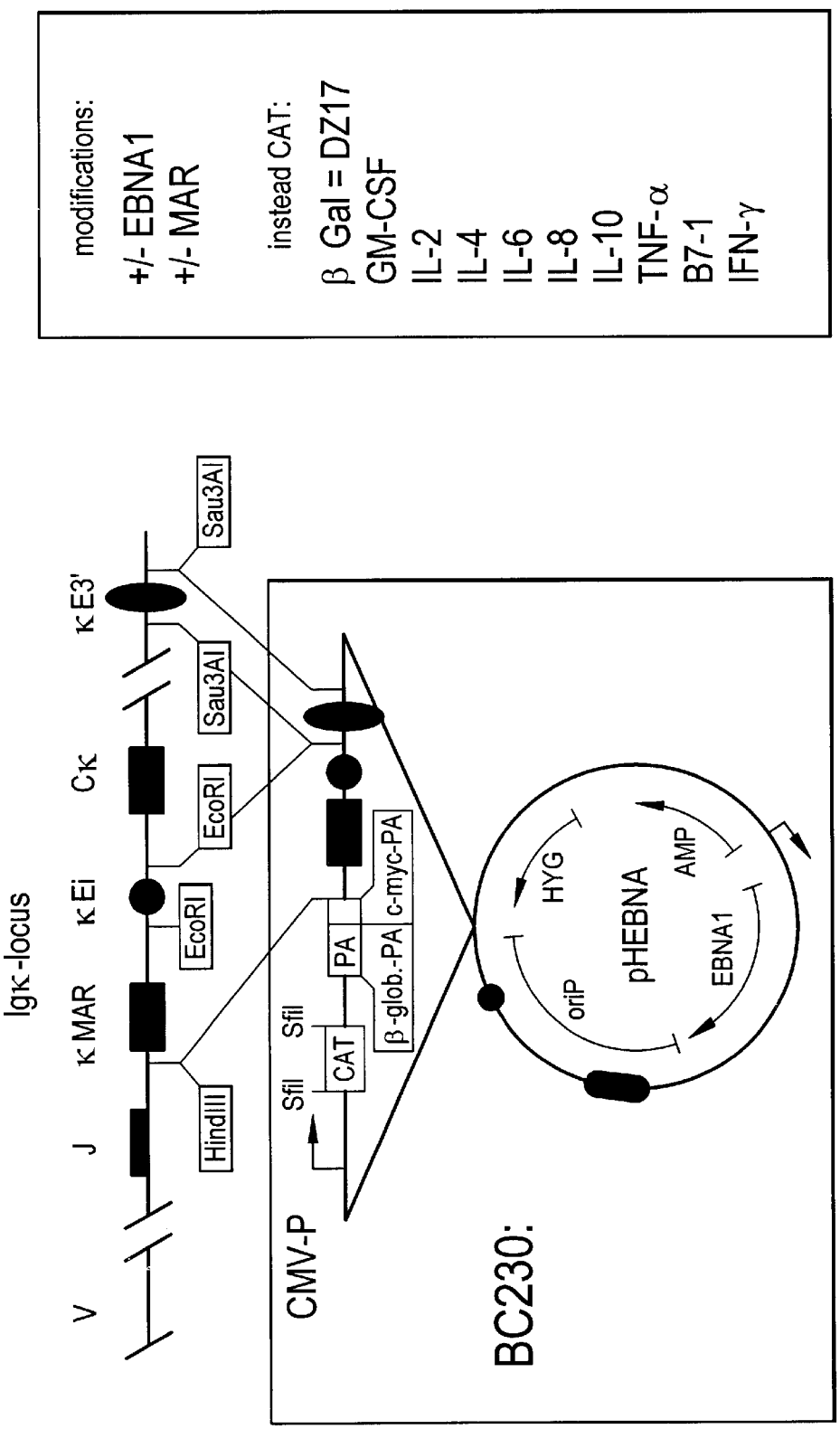

FIG. 1 Structure and Construction of the Vectors of the present Invention

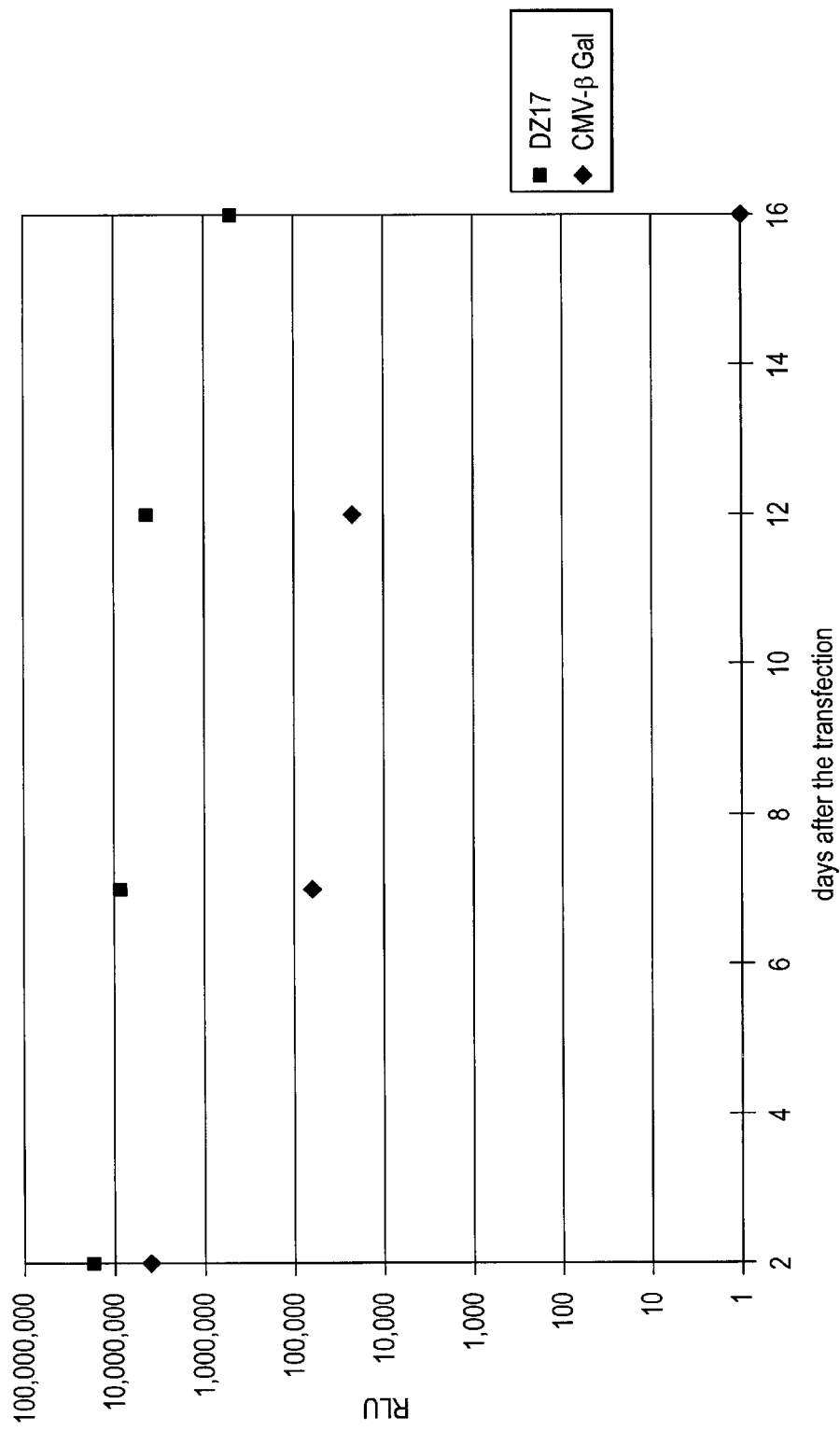

GENE CONSTRUCT AND ITS USE

This application is a continuation of U.S. application Ser. No. 08/713,059, filed Sep. 12, 1996 (now abandoned). Priority is claimed under 35 U.S.C. 119 to German patent application number 19541450.0 filed Nov. 7, 1995.

The present invention relates to a gene construct, a pharmaceutical preparation and their use.

The beginning of the era of gene therapy in medicine has been marked by the successful gene transfer of the adenosine desaminase gene to a child with severe immunodeficiency. To date findings coming mainly from animal experiments indicate that this form of therapy is not only useful in the correction of genetically caused diseases but also in the therapy of malignant neoplasias (Culver and Blaese, 1994).

The methods up to now being in the test phase are aimed at either a direct destruction or at least "normalization" of the tumor cell, or at the activation of an immune reaction directed against the tumor. The destruction by the transfer of so-called suicide genes or the normalization by the transfer of tumor suppressor genes requires the gene transfer being performed with high efficiency. The direct intratumour transfer of murine cell lines producing retroviruses containing the suicide gene thymidine kinase of herpes virus has been already performed in the case of multiform glioblastoma (Culver and Van Gilder, 1994).

As long as there is no efficient system available to achieve targeted gene transfer to all tumor cells in vivo, approaches involving the immune system in tracking down and destroying all tumor cells seem the most promising. However, a prerequisite of these approaches is the fundamental capability of the immune system to recognize the tumor cells by means of tumor-specific antigens, which appear on tumor cells and not on normal cells (Boon et al., 1994). For example, these tumor-specific antigens include viral gene products (e. g. gene products of the human papilloma virus in genital tumors) or mutationally altered oncogene products (e. g. the ras gene product or the tumor-specific bcr-abl fusion protein). Further suitable candidates for tumor specific antigens are the so-called idiotypes, i. e. immunoglobulins or T cell receptors on the cellular surfaces of B or T cell derived tumors. Recently, the identification of a plurality of tumor-associated antigens has been carried out, for example in malignant melanoma. These genes, however, are not exclusively expressed by the tumor, but to a small extent also by other somatic cells, such as melanocytes. The knowledge of tumor-specific or tumor-associated antigens, respectivly, is probably about to increase sharply because of the recent successful recovery and analysis by biochemical methods of the peptides presented by a tumor MHC complex (Mandelboim et al.; Cox et al., 1994).

Already in the mid-eighties, using an approach employing experiments on laboratory animals tumor cells were observed to loose their tumorigenicity in the syngeneic animal if the tumor cells were transfected with a cytokine expression vector (e. g. IL-2) by. gene transfer (Pardoll, 1993). This effect has also been observed in the case of a mixture of modified (i.e., cells that contained the expression vector) and non-modified cells. The local production of an immunostimulatory cytokine in a subset of the tumor cells is obviously capable of causing an immune reaction directed against the wild-type tumor. One of the most extensive studies of this kind using the murine malignant melanoma model B-16 showed retroviruses transducing GM-CSF, IL-4, and IL-6 to be most effective (Dranoff et al., 1993). The outcome of these observations was that a number of clinical studies on the subject of intratumour transfer of cytokines have been entered or are presently being entered worldwide (Foa et al., 1994). Generally, the protocols entail an ex vivo gene transfer into tumor cells which have been established in vitro for a short time period. In most of the protocols amphotrophic retroviruses are employed as vectors. After viral gene transfer, the cells are reimplanted into the patients. They can be irradiated prior to reimplantation. These approaches are, however, strongly limited by the technical difficulties of culturing the tumor cells in vitro even for a short time period. Therefore, a modification of this approach entails transducing or transfecting, respectively, either tumor infiltrating lymphocytes (TIL) (Treisman et al., 1995) or autologous fibroblast cells instead of the tumor cells themselves.

A further approach also referring to observations obtained from animal experiments in the eighties has been developed by Gary Nabel and already converted into a clinical protocol (Nabel et al., 1993; Plautz et al., 1993). This approach assumes that artificial allogenization of a subset of the tumor cells by the transfer of transplantation antigens may be sufficient to induce an immune reaction of the organism against the unmodified tumor cell. This protocol entails the direct transfer of an HLA B7 expression construct into the tumor using liposomes. Repeated injection of the HLA B7 gene construct into skin metastases of a moribund patient brought about regression of another untreated metastasis and of a pulmonary mestastasis, respectively (Nabel et al., 1993).

Many in vivo tumor cells lack the B7 surface antigen mediating co-stimulatory signals for T cell recognition. Therefore, attempts are made to stimulate the production of this signalling molecule in tumor cells by gene transfer (June et al., 1994; Li et al., 1994).

The aforementioned approaches to solve the problems bear the following disadvantages:

Retroviral Vectors

An advantage of amphotropic retroviruses is that integration of the proviral DNA into the target cell and the viral promoter/-enhancer combination generally permit a stable expression level during several cell divisions. The essential step of integration, however, bears the danger of insertional mutagenesis. Moreover, so-called "packaging" cell lines produce relatively small amounts of recombinant virus which to date fail to be enriched because of their lability. Therefore, direct intratumour gene transfer is only possible using virus producing cells. Release of infectious virus in the target organism, however, may lead to infection of other dividing cells, such as intestinal epithelium or hematopoietic stem cells, after hematogenous transmission.

Direct Intratumour DNA Transfer

The liposome-mediated direct incorporation of DNA has been demonstrated successfully using the endothelium of large blood vessels (Ohno et al., 1994). An advantage of this approach is that it lacks the risk of insertional mutagenesis as well as of the undesirable remote effect; but this approach achieves only transient expression of the incorporated gene construct in dividing tissue because the DNA generally fails to be integrated or replicated.

Cell Culture of Tumor Cells and Ex VIVO Transfection

One of the main technical obstacles is the in vitro culturing of tumor cells of every single patient. The performance of gene transfer into tumor cells cultured for a relatively short time period requires extraordinary experimental skills and is successful only in a portion of the cases. To date, infection with recombinant retroviruses represents the technique of choice for a gene transfer into this kind of cells.

EBV, EBV-derived Vectors, and EBV-immortalized Cells

EBV is present in lymphoblastoid cell lines (LCLs) in a state of latency. That means only a very small percentage of the infected cells produces infectious virus. In the state of latency, only six nuclear localized proteins (EBNA1, 2, 3A, B, C, LP) and two membrane-bound proteins (LMP and TP) of the virus are expressed. Generally, the EBV genome is present in the infected cell in episomal form in 10 to 100 copies. In the state of latency, the replication of the viral genome starts at an origin of replication (orip) (Yates et al., 1984). Maintenance of the episomal replication further requires binding of the EBNA1 protein to the oriP (Yates et al., 1984). The EBV-derived vectors consist of pBR sequences, oriP, an EBNA-1 expression cassette, and a selection marker specific for eukaryotic cells (e. g. the hygromycin resistance gene). Furthermore, these vectors have the capacity for additional 20 to 30 kb of foreign sequences. Constructs based on these vectors (i) show very much better "retention" in the cell even in the absence of selection (Middleton and Sugden, 1994); (ii) allow controlled expression without positional effects, and (iii) bear a substantially decreased risk of insertional mutagenesis. The efficiency of these vectors compared to mere plasmid vectors in obtaining stably transfected cells is substantially higher.

More than 95% of adult humans are infected by EBV. The primary infection occurs either asymptomatically or in the form of an infectious mononucleosis. The immunological control of the virus-infected cells in vivo has been very well investigated. The various latent gene products of the virus are recognized by specific cytotoxic T cells. Only in the state of extreme immunosuppression, e. g. as observed with AIDS patients or iatrogenically induced in transplant recipients, is there the possibility of polyclonally proliferating EBV-positive cells.

Enhancement of Gene Expression by Immunoglobulin Regulatory Elements

The synergistic way of function of the three regulatory elements (κMAR, κEi, κE3') of the immunoglobulin κ locus has first been demonstrated in the case of activation of the c-myc promoters P1 and P2 (Polack et al., 1993; Hörtnagel et al., 1995). In a chromosomal translocation observed in Burkitt lymphoma (BL) a co-localisation of the c-myc gene and the region of the human immunoglobulin κ locus located 3' of the "κ joining region" occurs, by which the c-myc gene is activated. A characteristic of this activation is an alteration in the usage of the promoters of the c-myc gene: the P1 promoter is used preferentially over the P2 promoter. In contrast, in normal non-transformed cells the P2 promoter is used preferentially. Furthermore, derepression of the c-myc gene on the level of transcriptional elongation is observed.

To study the mechanism of c-myc activation by t(2;8) translocation the interaction of the c-myc gene with several regions of the Igκ locus was examined. As a technique the stable infection of BL cells by episomally replicating EBV derived vectors has been selected. Into these vectors the c-myc gene was cloned under the control of two regions of the IgK locus. One of these regions extends from the J region up to about 1,2 kb 3' from the constant region (Cκ) while the second region encompasses the κ3'E located 12 kb 3' of Cκ. Measurement of the c-myc expression obtained by this construct and by several shortened forms (deletions) resulted first in the observation that these regions are necessary and sufficient for the BL-specific activation of the c-myc gene (Polack et al., 1993). By further deletions the responsibility of three elements of the Igκ locus, κMAR, κEi, and κE3', for the activation of the c-myc gene could be demonstrated (H örtnagel et al, 1995). Furthermore, the chromatin structure of the contructs stably introduced into BL cells was examined by DNaseI mapping of hypersensitive sites (HSS). The typical HSSs were formed in the 5' region of the c-myc gene as well as in portions of the Igκ locus. This demonstrates the formation of a normal chromatin structure on the extra-chromosomally replicating constructs.

Utilization of the Igκ elements in association with an episomal vector shows:
- a synergistic activation of a heterologous promoter (c-myc) by the Igκ elements;
- a large capacity of the episomal vectors;
- the formation of a regular chromatin structure.

The constructs described in the publication by Hörtnagel et al., 1995, were deletion constructs for the determination of regions of Ig which are essentially necessary for c-myc activation. It does not suggest the gene constructs according to the present invention containing the elements in a functional arrangement, and the use of the gene constructs according to the present invention.

One problem of the present invention to provide a gene construct for gene therapy avoiding the aforementioned disadvantages known from the state of the art.

This aim is achieved according to the invention by a gene construct containing, in functional association, at least:

(a)
- (i) a combination of two enhancer elements of the immunoglobulin κ locus, namely the κ intron enhancer (κEi) and the κ 3' enhancer (κE3'); or
- (ii) a combination of two enhancer elements of the immunoglobulin heavy chain μ locus, namely μEi and the μE3' enhancer region located 3' of Cα; or
- (iii) a combination of one or more of these enhancer elements of (ii) together with one or more of the aforementioned elements of the immunoglobulin κ locus; or
- (iv) the single enhancer element of the immunoglobulin λ locus; or
- (v) a combination of this enhancer element of (iv) together with one or more of the aforementioned elements of the immunoglobulin κ locus; or
- (vi) a combination of this enhancer element of (iv) together with one or more of the above elements of the immunoglobulin heavy chain μ locus; and further (b) a promoter;

(c) a gene of interest, selected from at least one element of the group, consisting of cytokine gene, viral antigen, cellular adhesion gene, tumor antigen, co-stimulatory signalling molecule gene, a HLA gene non-identical with the recipient, and β-galactosidase gene; and (d) a polyadenylation site (PAA).

Preferably, the gene construct according to the present invention contains the following combinations of regulatory elements:

κEi and λE, μEi and κE3', μEi and μE3', κEi and μE3', μEi and λE, κMAR and κEi and κE3', λE and κE3', λE and μE3'.

In a further preferred embodiment the gene construct of the present invention contains the immunoglobulin κ matrix attachment region (κMAR) or the immunoglobulin μ matrix attachment region (μMAR) in addition to one or more of the aforementioned enhancer elements or the combinations of enhancer elements.

The gene construct of the present invention is useful for gene therapy of diseases of the B cell system.

Preferably, the gene of interest may be the B7-1 or the B7-2 gene.

The gene construct of the present invention preferably contains sequences derived from EBV vectors, mini EBV vectors, bacterial vectors, from retroviruses, from adenovirus-associated viruses, from adenoviruses, or from vaccinia viruses. Further, it preferably contains sequences derived from bacterial vectors. In one embodiment of the invention, the sequence derived from EBV vectors or mini EBV vectors is the origin of replication (oriP).

In a preferred embodiment, the gene construct of the present invention additionally contains the EBNA1 expression cassette. Further, the gene construct of the present invention may additionally contain a marker gene, preferably being a resistance gene. This resistance gene is selected from resistance genes known as such. For example, an ampicillin resistance gene or a hygromycin resistance gene or a neomycin resistance gene may be employed.

The bacterial vector sequence may be chosen from any vector sequence known as such. Preferably, it is derived from pBR vectors.

In a particularly preferred embodiment, the gene construct of the present invention comprises EBV-derived vector sequences with or without the EBNA1 gene. Reference is made here to the complete contents of the publication of Sugden et al., 1985, and it shall be incorporated into this application for the completeness of the disclosure.

The promoter may be selected from any promoter capable of expressing the gene of interest in a selected cell. Preferably, the promoters of the group of a cell specific promoters, cytomegalovirus (CMV) promoter, tk and β globin promoters may be used.

The polyadenylation site may be derived from those sequences generally employed as a polyadenylation site. A representative polyadenylation site is the human β globin gene polyadenylation site or the SV 40 polyoma virus polyadenylation site.

The gene construct of the present invention allows the expression of a gene including therapeutically useful genes in a host cell. The protein encoded by the gene can then be produced by culturing the host cell under conditions that allow expression of the gene. Preferably, these therapeutically useful genes are expressed in B cells, B cell-derived cells, such as B cell tumor cells or cells immortalized by EBV or mini EBV, following successful gene transfer for the purpose of therapy of malignant and viral diseases.

Examples of the genes which may be expressed by the gene construct according to the invention are the cytokine genes, selected from the group of IL-2, -4, -6, -7, -8, -10, GM-CSF, G-CSF, TNF alpha, MCP 1, interferon gamma.

In a further embodiment of the present invention, into the construct of the present invention are inserted as a gene of interest a tumor antigen selected from the group of antigens members of human papilloma virus (HPV), melanoma-associated antigens, of the MAGE, BAGE, and GAGE gene family, the gp100, the idiotypes of T cell or B cell receptors of tumors, and mutated oncogenes. Particularly, the tumor antigens may be tumor-associated or tumor-specific antigens.

Preferably, the aforementioned tumor antigens are mutated oncogenes, such as ras genes or p53 genes or the derivatives thereof. The antigen associated with malignant melanoma is preferably the tyrosinase gene. Further genes of interest useful in the present invention are well-known to one skilled in the art and may be selected dependent on the disease to be treated.

The present invention also comprises such prokaryotic cells and eukaryotic cells transfected by one of the gene constructs of the present invention so as to contain the gene construct in an integrated or episomal, i. e. non-integrated, form. Preferably, the prokaryotic cell employed is an *E. coli* cell, and the eukaryotic cell employed is a B cell immortalized by EBV or mini EBV.

Preferably, the gene construct according to the present invention may contain as a gene of interest the viral antigens of HIV, CMV, HTLV1, and HPV, wherein said antigens are capable of inducing an immune reaction against the virus-infected cell.

The gene constructs according to the -invention may be used in the form of a pharmaceutical preparation further containing conventional carriers and/or excipients well known as such.

Preferably, the gene constructs of the invention are present in the pharmaceutical preparation according to the invention in liposomes or liposome-like structures.

In a further embodiment of the invention, the gene construct of the invention lacks a c-myc tumor antigen.

In a preferred embodiment of the invention there is provided a pharmaceutical preparation containing the gene construct of the invention in an effective amount together with conventional carriers and/or excipients.

In a further preferred embodiment of the present invention there is provided a pharmaceutical preparation containing primary B lymphocytes or fibroblast cells immortalized by EBV or mini EBV and comprising the gene construct of the present invention in an effective amount together with conventional carriers and/or excipients.

In a further preferred embodiment there is provided a pharmaceutical preparation containing primary B lymphocytes or fibroblast cells immortalized by EBV or mini 22V and comprising the gene construct of the present invention together with autologous T cells in an effective amount and conventional carriers and/or excipients.

In a further preferred embodiment there is provided a pharmaceutical preparation containing autologous T cells stimulated and expanded ex vivo using primary B lymphocytes or fibroblasts immortalized by EBV-or mini EBV and comprising the gene construct according to the invention.

By using an EBV-derived vector in combination with three specific regulatory elements of the immunoglobulin kappa locus, namely the matrix attachment region, the intron enhancer, and the 3' enhancer, a therapeutically beneficial gene can be specifically expressed in B cells over a prolonged time period. A further advantage of the use of the gene constructs of the invention is the ommission of the culturing of primary B cells, which is very complicated experimentally since immortalized cells (LCL cells) of almost any individual can be obtained by infection of peripheral B cells with EBV or mini EBV (see review n: Rogers et al., 1992). The establishment of these LCLs is much less complicated experimentally than the culture of primary tumor cells.

Figure 2:
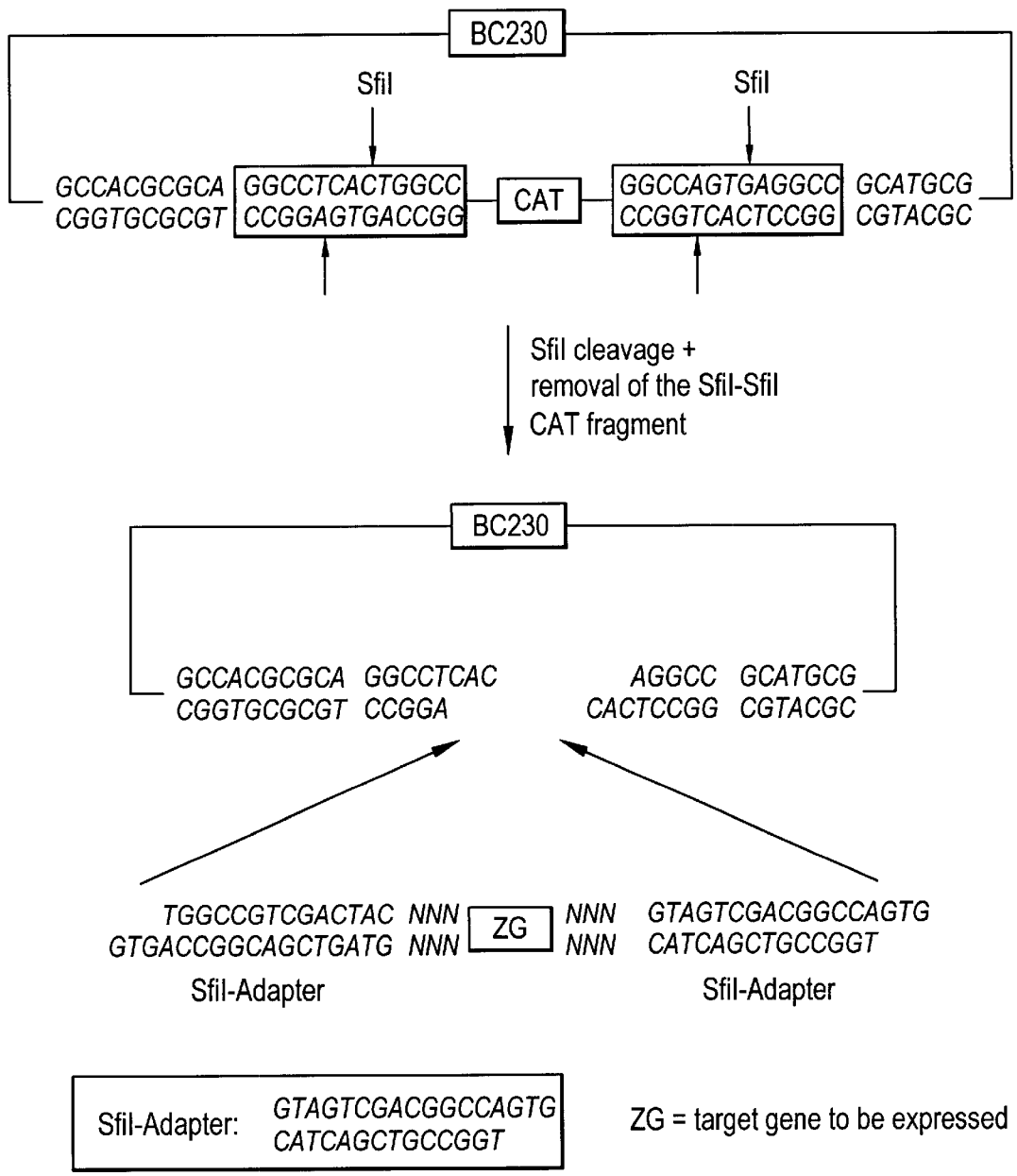

In the following the present invention will be explained in more detail refering to the attached Figures. Among the Figures :

FIG. 1: represents the construction and the structure of a gene construct according to the invention;

FIG. 2: represents schematically the cloning of one of the genes to be expressed into vector BC230 or into a vector derived therefrom;

FIG. 3: represents the expression of β-galactosidase in Burkitt's lymphoma (BL) cells transfected with DZ17 and CMV β-gal, respectively.

Preferably, the gene constructs according to the invention are based on vectors derived from Epstein Barr virus and containing the sequences for oriP, the EBNA1 expression cassette, resistance markers and, optionally, further pBR sequences.

Preferably, the vectors according to the present invention further contain a combination of different regulatory elements of the immunoglobulin kappa locus: the matrix attachment region (MAR), and the enhancer elements located in the intron (Ei) of the kappa locus as well as 12 kb 3' (E3') of the Ig kappa gene constant region.

Preferably, the promoter region of the expression cassette is derived from human cytomegalovirus (immediate early gene; CMV-P). Preferably, the polyadenylation site is derived from the human β globin gene. Further useful promoters are minimal promoters, such as the tk or the β globin promoter.

In a preferred embodiment the activity of the vector shall be restricted to B cells in order to meet safety requirements. For example, this can be achieved by introduction of the c-myc P1 promoter instead of the CMV promoter. An almost complete lack of activity of this promoter in the absence of enhancer could be demonstrated. Because of this property, this promoter appears to be particularly useful to achieve the restriction of the activity of the vector to B cells by using a B cell specific enhancer.

The sequence of the EBNA1 expression cassette is known. This expression cassette may be cloned into an EBV derived vector, as for example described by Yates et al., 1985. Particularly useful is the region between the oriP and the hygromycin resistance gene cassette (HYG).

The vectors of the present invention may carry as a reporter gene either the β galactosidase gene or the chloramphenicol acetyl transferase gene, and said gene may be under the control of the CMV promoter. Vectors useful for the transfection of EBV negative cells are such vectors carrying the expression cassette for the EBNA1 gene.

Different cytokine genes or tumor antigens may be cloned into the cloning sites from SfiI 842 through SfiI 862 or NaeI at 850. Cytokine genes useful in the present invention are for example: IL-2, -4, -6, -7, -8, -10, GM-CSF, G-CSF, TNF alpha, MCP 1, interferon gamma.

The viral antigens or tumor antigens which may be used include: viral antigens of viruses associated with the formation of tumors, such as antigens of the human papilloma virus (HPV), antigens associated with malignant melanoma, such as tyrosinase, the MAGE, BAGE and GAGE gene family, and the gp100, the idiotypes of T cell receptors or B cell receptors of tumors derived from T cells or B cells, mutated oncogenes, such as the ras gene or the p53 gene, and the like. Further, the viral antigens which may be used include antigens of HIV and of CMV capable of inducing an immune reaction against the virus-infected cell.

For direct gene transfer or ex vivo gene transfer into tumor cells an HLA gene may also be used which is foreign to the recipient, such as the HLA B7 gene or the gene of the co-stimulatorily acting B7 molecule.

Referring to FIG. 1, the construction of one of gene constructs of the invention, namely of the vector BC230 is described in the following by way of example.

The construction of BC230 was performed starting from the Epstein Barr virus derived vector p201 (pHEBNA) described by Sugden et al. (1985). Together with portions of pBR322 and a hygromycin resistance gene expression cassette (HYG), this vector contains the origin of replication (orip) of EBV (sequence position 7333 up to 9109 of B95-8 EBV [=designation in the EMBL data bank] as well as a 2,6 kbp region (sequence position 107567 up to 110176 of B95-8) coding for the EBNA1 (Epstein Barr virus nuclear antigen 1) gene.

Then, between the oriP and the hygromycin resistance gene were cloned the promoter/enhancer region of human cytomegalovirus (sequence position 467 up to 1218 of HEHCMVP1 [=designation in the EMBL data bank]), the chloramphenicol acetyl transferase gene (CAT) (sequence position 452 to 1240 of BLCAT3DNA [=designation in the EMBL data bank]) and the polyadenylation site of the rabbit beta globin gene (sequence position 31393 to 32554 of OCBGLOO1 [=designation in the EMBL data bank]).

Between the β globin polyadenylation signal and the hygromycin resistance gene were introduced part of the polyadenylation site of c-myc (sequence position 7800 to 8056 of HSMYCKOB [=designation in the EMBL data bank]), the matrix attachment region (κMAR), the adjacent intron enhancer (κEi), and the 3' enhancer (κE3') located 3' of the constant region of the human kappa gene. The κMAR element has been defined as a HindIII-EcoRr fragment (sequence position 3237 to 3447 of HSIGK1 [=designation in the EMBL data bank]), and the κEi has been defined as an EcoRI-EcoRI fragment (sequence position 3447 to 4153 of HSIGK1 [=designation in the EMBL data bank]) (H örtnagel et al., 1995). The κE3' is represented by a Sau3AI-Sau3AI fragment being 1169 bp in length.

The CAT gene may be removed by restricting with restriction enzyme SfiI. The resulting ends of the vector fragment (BC230vec) are non-compatible and therefore are not capable of being ligated with each other. Therefore, treatment of the vector fragment with phosphatase (CIP; calf intestinal phosphatase) can be omitted. A target gene to be expressed being present as a "blunt end" fragment (either by digestion with suitable restriction enzymes [enzymes generating "blunt ends"], or by digestion with restriction enzymes followed by treatment with Klenow polymerase to fill in protruding ends) may be cloned into BC230vec using ligation with two SfiI adapters (see FIG. 2). Because of the incompatibility of the protruding ends generated on one side of the adapter no undesired circular molecules are formed during ligation. A further advantage of this procedure is that the gene segment to be cloned may contain the recognition sequence of SfiI enzyme. Therefore, restriction of the gene segment to be cloned with SfiI prior to ligation as it is necessary in the preparation of a "classical" linker ligation is dispensable.

By modification of the BC230 vector the following variations were generated:
a. without MAR element: the HindIII-EcoRI fragment was removed (BC229);
without EBNA1 gene for expression in EBV positive cells (BC243);
inclusion of the β galactosidase gene instead of the CAT gene (DZ17);
the genes which may be cloned into the BC230 vector include for example the following : IL-2, -4, -6, -8, -10, GM-CSF, B7-1, IFN γ, TNF α; those vectors are referred to as BC219.

EXAMPLE 1

In the FIG. 3 the advantages of the utilization of the vector of the invention are exemplified by DZ17 containing the β galactosidase gene.

BL cells (Raji) were transfected transiently by electroporation with DZ17 vector and the CMV β-gal construct (lacking the enhancer cassette and portions of EBV; β-gal=β galactosidase). Afterwards, the cells were cultered for 16 days in the absence of hygromycin (i. e. in the absence of selection). After 2, 7, 12, and 16 days aliquots of the cells were recovered and the expression of β galactosidase was determined. FIG. 3 shows the results of this assay. While, after two days the expression of the two plasmids differed by about a factor of 4, a significant difference was observed already after 7 days. After 16 days, no expression of β galactosidase in the cells transfected by CMV β-gal could be detected. In cells transfected by DZ17, a maintenance of β galactosidase activity could be detected which was 10 times lower but still high. This result has to be interpreted in a way that the vector of the invention fulfils the property of being retained in cells achieving a high expression and ensuring the expression over a prolonged time period.

EXAMPLE 2

Efficiency of Transfection

An EBV-positive (BL60) and an EBV-negative (BJAB) human lymphoma cell line were chosen as a target cell for the comparison of a conventional integrating vector (pKEX, Rittner et al., 1991) and vector BC219, a derivative of BC230 lacking the CAT gene. BC219 was used instead of BC230 because BC230 expresses chloramphenicol acetyl transferase (CAT). High doses of this enzyme in the cell may exert toxic activity and thereby complicate the comparison. pKEX contains the CMV promoter/enhancer region, a SV40-derived polyadenylation site, the hygromycin resistance gene expression cassette, and a portion of pBR including the origin of replication for multiplication in bacteria. This vector as well as its derivatives have to be integrated into the cellular genome for stable replication within the target cells.

DNA from BC219 and pKEX was introduced into both cell lines by electroporation (method described by Polack et al., 1991). After 24 h in the absence of selection pressure, the cells were seeded at a density of $2\times10^5$ cells/ml into a 96-well cell culture plate in a volume of 100 µl/well under selective conditions (400 µg/ml hygromycin). The samples showing cellular proliferation were counted, grown, and tested further. The following table shows the results of an experiment of the aforementioned type

TABLE 1

| Cell line | Vector | Transfection efficiency Growth per $1 \times 10^6$ cells plated |
|---|---|---|
| BJAB | pKEX | 10 |
|  | BC219 | 100 |
| BL60 | pKEX | 0.3 |
|  | BC219 | 500 |

This result can be explained in a way that stable transfectants can be prepared much more readily using the BC230 derivative BC219.

EXAMPLE 3

Cytokine Expression using BC230 Derivatives

As shown in the FIG. 1, the cDNAs of TNFα, GM-CSF and IL6 were cloned into vector BC230 and into its derivative BC219, and into pKEX, respectively. Using these constructs, different transformants were generated after stable transfection and selection with hygromycin. The production of the different cytokines was determined in the cellular supernatant of the different transfectants using a commercially avaible ELISA (Biermann Co., Bad Nauheim, Germany). The BL60 cells fail to produce any of these cytokines either spontaneously or after transfer of BC230 or pKEX. In any of these cases, transfectants generated by the integrating vectors (pKEX and derivatives) failed to produce a detectable amount of TNFα, GM-CSF or IL6, respectively.

All of the ten different sublines generated by each of the three cytokine vectors based on vector BC219 secreted about the same amount of cytokine into the supernatant. The variation in the cytokin production of the individual transfectants is listed in the following table:

TABLE 2

| Cell line | Construct | Number of clones analysed | Cytokine production (variation) |
|---|---|---|---|
| BL60 | pKEX-CAT | 10 | not detectable |
|  | pKEX-IL6 | 5 | n. d. |
|  | pKEX-TNF α | 9 | n. d. |
|  | BC230 | 10 | n. d. |
|  | BC219-TNF α | 10 | 1500–2000 pg/ml TNF α |
|  | BC219GM-CSF | 10 | 700 pg/ml GM-CSF |
|  | BC219-IL6 | 10 | 900–1000 pg/ml IL-6 |

After transfer either ex vivo or in vivo, EBV-derived vectors have the capability of being retained within cells in the absence of selection. Therefore, expression of genes transferred by these vectors occurs over a prolonged time period. Thus, the direct liposome-mediated intratumour transfer of a construct expressing for example GM-CSF, e. g. into a B cell lymphoma in order to stimulate the body's own defenses against the tumor cells, is an effective therapeutic.

EBV Immortalized B Cells as Target Cells for Gene Transfer

In vitro culturing of tumor cells is only successful for a part of the tumor patients. By using EBV, immortalized B cells of any individual can be produced in unlimited amounts. These cells can be made to produce messenger substances (cytokines) effective in immunomodulation by gene transfer with the aforementioned construct. To stimulate an immune reaction directed against a tumor, the cells generated in this manner can be inoculated, e. g. subcutaneously, directly into the tumor as well as in combination with tumor cells. For safety, these cells may be prevented from further proliferation by irradiation prior to transplantation.

Further, EBV immortalized cells may be made to express viral or tumor antigens by transfection of the corresponding gene constructs. These antigens should be presented by the cells in an MHC restricted manner. Therefore, those cells are useful for the stimulation of autologous T cells recognizing these antigens. The thereby stimulated T cells may be expanded using those antigen-presenting cells and IL-2. After transfer, the expanded T cells in vivo will specifically attack the virally infected cells or the tumor cells expressing the antigen.

Using EBV establishment of cell lines from any individual becomes relatively simple. These cells can be provided ex vivo with gene constructs and then retransplanted into the syngenic individual. In an adoptive immune therapy, the cells may be employed either as producers of cytokines or as antigen-presenting cells. In all embodiments, EBV may also be replaced by mini EBV.

Thus, in conclusion, a vector is. provided preferably based on EBV which allows the achievement of a high and persistant expression, i. e. a stable expression, in cells, particularly in B cells, which expression is an improvement over all other known vector systems. Genes of therapeutical value such as cytokine genes or tumor antigens can be stably incorporated into the B cells to be treated and used in the therapy of malignant and viral diseases of man, in particular of B cell tumor-associated diseases. All publications referred to herein are hereby expressly incorporated by reference in their entirety. The gene constructs of the present invention are especially useful for the use in gene therapy.

What is claimed is:

1. A gene construct for the expression of a polypeptide, comprising:
   (a) an enhancer comprising an element or combination of elements, wherein said element or combination of elements is selected from the group consisting of:
      (i) a combination comprising the following elements obtained from the immunoglobulin κ locus: the κ intron enhancer (κEi), the κ 3' enhancer (κE3'), and the immunoglobulin κ matrix attachment region (κMAR);
      (ii) a combination comprising the following elements obtained from the immunoglobulin heavy chain μ locus: the μ0 intron enhancer (μEi) and the μ 3' enhancer obtained from a region located 3' of Cα (μE3');
      (iii) a combination of
         one or more elements selected from the group consisting of κEi and κE3+ and
         one or more elements selected from the group consisting of μEi and μE3';
      (iv) the enhancer element of the immunoglobulin λ locus (λE);
      (v) a combination of
         λE and
         one or more elements selected from the group consisting of κEi and κE3'; and
      (vi) a combination of
         λE and
         one or more elements selected from the group consisting of μEi and μE3';
   (b) a promoter operably linked to said enhancer;
   (c) a nucleotide sequence operably liked to said promoter, said nucleotide sequence encoding a polypeptide selected from the group consisting of: a cytokine, a viral antigen, a cellular adhesion protein, a tumor antigen with the proviso that the c-myc-antigen is excluded, a co-stimulatory signalling molecule, an HLA antigen, and β-galactosidase; and
   (d) a polyadenylation site (PAA) operably linked to said nucleotide sequence.

2. The gene construct according to claim 1, wherein said enhancer comprises a combination of enhancer elements selected from the group consisting of:
   κEi and λE, μEi and κE3', μEi and μE3', κEi and μE3', μEi and λE, the immunoglobulin κ matrix attachment region (κMAR) and κEi and κE3', λE and xE3', and λE and μE3'.

3. The gene construct according to claim 1, wherein said gene construct additionally comprises the immunoglobulin μ matrix attachment region (μMAR).

4. The gene construct according to claim 1, wherein said polypeptide is an HLA antigen.

5. The gene construct according to claim 4, wherein said HLA antigen is HLA B7.

6. The gene construct according to claim 1, wherein said gene construct further comprises an additional sequence obtained from a source selected from the group consisting of an EBV vector, a mini EBV vector, a bacterial vector, a retrovirus, an adenovirus-associated virus, an adenovirus and a vaccinia virus.

7. The gene construct according to claim 6, wherein said additional sequence is derived from an EBV vector and comprises the origin of replication of EBV (oriP) and a resistance gene said gene construct additionally comprising a sequence derived from a pBR vector.

8. A gene construct according to claim 7, additionally comprising an expression cassette for EBNA1.

9. The gene construct according to claim 6, wherein said additional sequence is selected from the group consisting of:
   (a) a sequence derived from an EBV vector consisting of the origin of replication (oriP), a sequence encoding EBNAI, and a sequence encoding a marker gene; and
   (b) a sequence derived from a pBR vector.

10. The gene construct according to claim 1, wherein said gene construct further comprises a marker gene.

11. The gene construct according to claim 10, wherein said marker gene is a resistance gene selected from the group consisting of an ampicillin resistance gene, a hygromycin resistance gene, and a neomycin resistance gene.

12. The gene construct according to claim 1, wherein said promoter is selected from the group consisting of a B cell-specific promoter, a cytomegalovirus (CMV) promoter, a tk promoter, a β globin promoter, and a c-myc P1 promoter.

13. The gene construct according to claim 1, wherein said polyadenylation site is derived from a source selected from the group consisting of a human β globin gene or an SV40 polyomavirus.

14. The gene construct according to claim 1, wherein said polypeptide is a cytokine selected from the group consisting of IL-2, -4, -6, -7, -8, -10, GM-CSF, G-CSF, TNT alpha, MCP 1, and interferon gamma.

15. The gene construct according to claim 1, wherein said polypeptide is a viral antigen selected from the group consisting of an HIV antigen, an HTLV1 antigen, an BPV antigen, and a CMV antigen.

16. A composition comprising a liposome or a liposome-like structure and the gene construct according to claim 1.

17. An isolated cell comprising the gene construct of claim 1.

18. The isolated cell according to claim 17, wherein said cell is an *E. coli* cell.

19. The isolated cell according to claim 17, wherein said cell is a eukaryotic cell.

20. The isolated cell of claim 19 wherein the gene construct is present in said cell in an integrated form in a chromosome of said cell.

21. The isolated cell of claim 19, wherein the gene construct is present in said cell in an episomal form.

22. A process for producing the polypeptide encoded by said gene construct, comprising culturing the cell of claim 21 under conditions whereby said polypeptide is produced by said cell.

23. The isolated cell of claim 19, wherein the cell is selected from the group consisting of a B cell and a fibroblast cell and wherein said cell is immortalized by EBV or mini EBV.

24. A process for producing the polypeptide encoded by said gene construct comprising culturing the cell of claim 17 under conditions whereby said polypeptide is produced by said cell.

25. The process of claim 24, wherein said cell is a eukaryotic cell.

26. A process for stimulating T cell growth in culture, comprising contacting a T cell with an immortalized cell immortalized by EBV or mini EBV, said immortalized cell selected from a primary B lymphocyte and a fibroblast, said immortalized cell comprising a gene construct according to claim 1, wherein said contacting is cared out for a time sufficient to stimulate the growth of said T cell.

27. The process of claim 26 wherein said gene construct was introduced into said immortalized cell by gene transfer.

28. A process for producing an insulated cell comprising a gene construct, said process comprising introducing the gene construct of claim 1 into said cell by gene transfer, wherein said cell is a primary B lymphocyte or a fibroblast, wherein said cell is immortalized by EBV or mini-EBV.

29. The gene construct according to claim 1, wherein said polypeptide is a co-stimulatory signaling molecule.

30. The gene construct according to claim 29, wherein said co-stimulatory signaling molecule is encoded by a gene selected from a B7-1 gene and a B7-2 gene.

31. The gene construct according to claim 1, wherein said polypeptide is a tumor antigen.

32. The gene construct according to claim 31, wherein said tumor antigen is selected from the group consisting of a tumor-associated antigen and a tumor-specific antigen.

33. The gene construct according to claim 31, wherein said tumor antigen is encoded by an oncogene.

34. The gene construct according to claim 31, wherein said tumor antigen is selected from the group consisting of ras, p53, derivatives of ras, derivatives of p53, and tyrosinase.

35. The gene construct according to claim 31, wherein said tumor antigen is selected from the group consisting of an antigen of the human papilloma virus (BPV), a malignant melanoma-associated antigen, a MAGE antigen, a BAGE antigen, a GAGE antigen, gp100, a tumor idiotype of a T cell receptor, a tumor idiotype of a B cell receptor, and a tumor antigen encoded by a mutated oncogene.

36. A process or producing a cell comprising a gene construct, said process comprising:
(a) immortalizing a primary B lymphocyte to produce an immortalized B lymphocyte; and
(b) introducing the gene construct according to claim 1 into said immortalized B lymphocyte.

* * * * *